United States Patent
Schäfer (10) Patent No.: US 11,219,425 B2
(45) Date of Patent: Jan. 11, 2022

(54) REDUNDANCY-WEIGHTED IMAGE RECONSTRUCTION FOR SHORT-SCAN X-RAY TOMOGRAPHY WITH AN OFF-CENTER X-RAY DETECTOR

(71) Applicants: KONINKLIJKE PHILIPS N.V., Eindhoven (NL); ION BEAM APPLICATIONS S.A., Louvain-la-Neuve (BE)

(72) Inventor: Dirk Schäfer, Hamburg (DE)

(73) Assignees: KONINKLIJKE PHILIPS N.V., Eindhoven (NL); ION BEAM APPLICATIONS S.A., Louvain-la-Neuve (BE)

( * ) Notice: Subject to any disclaimer, the term of this patent is extended or adjusted under 35 U.S.C. 154(b) by 0 days.

(21) Appl. No.: 16/470,587

(22) PCT Filed: Dec. 19, 2017

(86) PCT No.: PCT/EP2017/083662
§ 371 (c)(1),
(2) Date: Jun. 18, 2019

(87) PCT Pub. No.: WO2018/115025
PCT Pub. Date: Jun. 28, 2018

(65) Prior Publication Data
US 2020/0085389 A1   Mar. 19, 2020

(30) Foreign Application Priority Data
Dec. 21, 2016  (EP) .................................... 16205791

(51) Int. Cl.
*A61B 6/03*   (2006.01)
*A61B 6/00*   (2006.01)
(Continued)

(52) U.S. Cl.
CPC ............ *A61B 6/5205* (2013.01); *A61B 6/027* (2013.01); *A61B 6/03* (2013.01); *A61B 6/035* (2013.01);
(Continued)

(58) Field of Classification Search
CPC ......... A61B 6/027; A61B 6/032; A61B 6/035; A61B 6/06; A61B 6/40; A61B 6/4021;
(Continued)

(56) References Cited

U.S. PATENT DOCUMENTS 6,542,573 B2 *  4/2003  Schomberg .......... G06T 11/005
                                                    378/19
6,546,068 B1 *  4/2003  Shimura ................ A61B 6/032
                                                    378/19
(Continued)

FOREIGN PATENT DOCUMENTS

| WO | 199517725 A1 | 6/1995 |
| WO | 2010109352 A1 | 9/2010 |
| WO | 2015073048 A1 | 5/2015 |

OTHER PUBLICATIONS

Ge Wang, X-ray micro-CT with a displaced detector array, Med. Phys. 29(7), Jul. 2020, 1634-1636.*
(Continued)

*Primary Examiner* — Allen C. Ho (57) ABSTRACT

The invention relates to off-center detector X-ray tomography reconstruction of an image of an object on the basis of projection data acquired during a rotation of an X-ray source and the off-center detector around the object in two rotational passes of less than 360°, wherein a focus point of the X-ray beam travels along largely overlapping arcs (401, 402) in the two rotational passes, the off-center detector being positioned asymmetrically with respect to a central of the X-ray beam and a direction of a detector offset being reversed between the passes. According to the invention,
(Continued)

redundancy weighting of the projection data with respect to a redundant acquisition of projection values during each of the rotational passes is made using a redundancy weighting function determined on the basis of a union of the arcs (401, 402).

20 Claims, 4 Drawing Sheets

(51) Int. Cl.
    *A61B 6/02*     (2006.01)
    *G06T 11/00*     (2006.01)
    *A61B 6/06*     (2006.01)
    *G01N 23/046*     (2018.01)

(52) U.S. Cl.
    CPC .............. *A61B 6/06* (2013.01); *A61B 6/40* (2013.01); *A61B 6/405* (2013.01); *A61B 6/4021* (2013.01); *A61B 6/4064* (2013.01); *A61B 6/4078* (2013.01); *A61B 6/4085* (2013.01); *A61B 6/42* (2013.01); *A61B 6/4208* (2013.01); *A61B 6/4233* (2013.01); *A61B 6/44* (2013.01); *A61B 6/4429* (2013.01); *A61B 6/4435* (2013.01); *A61B 6/4441* (2013.01); *A61B 6/4447* (2013.01); *A61B 6/52* (2013.01); *A61B 6/5211* (2013.01); *A61B 6/5258* (2013.01); *A61B 6/547* (2013.01); *G01N 23/046* (2013.01); *G06T 11/005* (2013.01)

(58) Field of Classification Search
    CPC ..... A61B 6/405; A61B 6/4064; A61B 6/4078; A61B 6/4085; A61B 6/42; A61B 6/4208; A61B 6/4233; A61B 6/44; A61B 6/4429; A61B 6/4435; A61B 6/4441; A61B 6/4447; A61B 6/4452; A61B 6/52; A61B 6/5205; A61B 6/5211; A61B 6/5258; G01N 23/046
    USPC ...... 378/4, 11, 15, 19, 210, 901; 250/370.09
    See application file for complete search history.

(56) References Cited

U.S. PATENT DOCUMENTS

| | | | |
|---|---|---|---|
| 6,944,260 B2* | 9/2005 | Hsieh | A61B 6/032 378/19 |
| 7,110,487 B2* | 9/2006 | Baba | G06T 11/005 378/11 |
| 7,394,923 B2* | 7/2008 | Zou | G01N 23/046 378/4 |
| 7,403,588 B2 | 7/2008 | Bruder | |
| 7,643,605 B2* | 1/2010 | Ning | A61B 6/502 378/4 |
| 7,751,524 B2* | 7/2010 | Horiuchi | A61B 6/032 378/4 |
| 7,760,852 B2* | 7/2010 | Chen | A61B 6/032 378/19 |
| 7,869,561 B2* | 1/2011 | Dafni | H01J 35/10 378/9 |
| 7,986,762 B2* | 7/2011 | Kunze | A61B 6/5241 378/11 |
| 8,094,774 B2* | 1/2012 | Noshi | G06T 11/006 378/15 |
| 8,199,873 B2* | 6/2012 | Star-Lack | A61B 6/5282 378/7 |
| 8,199,879 B2* | 6/2012 | Star-Lack | G06T 11/005 378/98.4 |
| 8,204,172 B1* | 6/2012 | Hsieh | A61B 6/037 378/8 |
| 8,204,173 B2* | 6/2012 | Betcke | A61B 6/5205 378/9 |
| 8,224,056 B2* | 7/2012 | Pack | G06T 7/11 382/131 |
| 8,306,304 B2* | 11/2012 | Noo | A61B 6/032 382/131 |
| 8,340,245 B2* | 12/2012 | Herranz | G01V 5/005 378/57 |
| 8,428,216 B2* | 4/2013 | Dennerlein | G06T 11/006 378/4 |
| 8,442,294 B2* | 5/2013 | Sonke | G06T 7/20 382/132 |
| 8,483,363 B2* | 7/2013 | Bertram | A61B 6/4035 378/157 |
| 8,660,235 B2* | 2/2014 | Koehler | A61B 6/4035 378/4 |
| 8,693,638 B2* | 4/2014 | Dafni | A61B 6/4021 378/124 |
| 8,731,267 B2* | 5/2014 | Nakanishi | G06T 11/005 382/131 |
| 8,761,478 B2* | 6/2014 | Hsieh | G06T 11/006 382/131 |
| 8,787,646 B2* | 7/2014 | Schaefer | G06T 11/005 382/131 |
| 8,824,765 B2* | 9/2014 | Dennerlein | G06T 11/006 382/131 |
| 8,861,674 B2* | 10/2014 | Koehler | A61B 6/469 378/4 |
| 8,948,337 B2* | 2/2015 | Pack | G06T 11/006 378/4 |
| 9,001,963 B2* | 4/2015 | Sowards-Emmerd | G06T 11/006 378/11 |
| 9,013,471 B2* | 4/2015 | Lauritsch | A61B 6/4458 345/419 |
| 9,123,156 B2* | 9/2015 | Takahashi | G06T 11/006 |
| 9,159,462 B2* | 10/2015 | Rossl | A61B 6/4035 |
| 9,406,121 B2* | 8/2016 | Goto | G06T 5/001 |
| 9,420,975 B2* | 8/2016 | Gutfleisch | A61B 6/4452 |
| 9,439,617 B2* | 9/2016 | Flohr | A61B 6/032 |
| 9,448,325 B2* | 9/2016 | Chen | G01T 1/2985 |
| 9,628,723 B2* | 4/2017 | Yu | A61B 6/582 |
| 9,636,079 B2* | 5/2017 | Bredno | A61B 6/42 |
| 9,655,568 B2* | 5/2017 | Ritschl | H05G 1/02 |
| 9,662,084 B2* | 5/2017 | Tang | A61B 6/5205 |
| 9,710,936 B2* | 7/2017 | Schretter | A61B 6/4452 |
| 10,123,763 B2* | 11/2018 | Kondo | A61B 6/548 |
| 10,210,633 B2* | 2/2019 | Yamakawa | G06T 5/002 |
| 11,045,151 B2* | 6/2021 | Jensen | A61B 6/4035 |
| 2005/0100124 A1 | 5/2005 | Hsieh | |
| 2009/0028288 A1 | 1/2009 | Horiuchi | |

OTHER PUBLICATIONS

M. Grass et al., Angular-weighted hybrid cone-beam CT reconstruction for circular trajectories, Phys. Med. Biol 46 (2001) 1595-1610.*

Dennis L. Parker, Optimal short scan convolution reconstruction for fan-beam CT, Med. Phys. 9 (2), Mar./Apr. 1982, 254-257.*

Xia, Yan et al "Dose Reduction Achieved by Dynamically Collimating the Redundant rays in Fan-Beam and Cone-Beam CT", IEEE 2013.

Herbst, Magdalena et al "Dynamic Detector Offsets for Field of View Extension in C-arm Computed Tomography with Application to Weight-Bearing Imaging", Medical Physics, vol. 42, No. 5, May 2015, pp. 2718-2729.

International Search Report and Written Opinion of PCT/EP2017/083662, dated Apr. 4, 2018.

Wesarg, S. et al "Parker Weights revisited", Medical Physics, vol. 29, No. 3, Mar. 2002.

Schafer, D. et al "FBP and BPF Reconstruction methods for Circular X-ray Tomography with Off-Center Detector", Medical Physics, vol. 38, No. 7, Jul. 2011.

(56) References Cited

OTHER PUBLICATIONS

Silver, Michael D. "A Method for Including redundant data in computer tomography", Medical Physics, vol. 27, No. 4, Apr. 2000, pp. 773-774.

* cited by examiner

REDUNDANCY-WEIGHTED IMAGE RECONSTRUCTION FOR SHORT-SCAN X-RAY TOMOGRAPHY WITH AN OFF-CENTER X-RAY DETECTOR

CROSS-REFERENCE TO PRIOR APPLICATIONS

This application is the U.S. National Phase application under 35 U.S.C. § 371 of International Application No. PCT/EP2017/083662, filed on Dec. 19, 2017, which claims the benefit of European Patent Application No. 16205791.3, filed on Dec. 21, 2016. These applications are hereby incorporated by reference herein.

FIELD OF THE INVENTION

The invention is related to a redundancy weighting for short scan off-center detector X-ray tomography. More specifically, the invention relates to a device and a method for off-center detector X-ray tomography reconstruction using redundancy weighting of projection data acquired using the off-center detector. Further, the invention relates to a computer program for carrying out the method.

BACKGROUND OF THE INVENTION

Modern X-ray tomography devices use X-ray sources which emit a diverging beam, such as a fan beam or a cone beam. The beam traverses an examination region including an object to be imaged, and is intercepted by a detector, which comprises an array of detector elements for detecting incident X-ray radiation. For each ray of the X-ray beam, the detector particularly measures a projection value or line integral value with respect to the line along which the respective ray travelled through the object to be imaged (or next to the object).

The detector is arranged at a fixed position opposite to the X-ray source and both the X-ray source and the detector are mounted on a rotatable gantry. During an X-ray tomography scan, the X-ray source and the detector rotate around the object in order to acquire a plurality of projection values for the object, which are then used in order to reconstruct a three-dimensional image of the object. In order to reconstruct an image of the complete object, projection values for all lines passing through the object have to be acquired in this process.

Conventionally, the X-ray source is rotated around the object in a full circle, i.e. on an arc covering 360°, in order to measure projection data for all lines passing through the object. In this case, each line is even sampled twice with rays travelling in opposite directions. These leads to a redundancy, which has to be taken account of in the reconstruction of the image of the object, e.g. by weighting each projection value with ½. In this case, the reconstruction is effectively made on the basis of the average of the redundant measurements.

However, it is likewise possible to measure projection values for all lines passing through the object without having to rotate the X-ray source around the object in a full circle. Rather, it can be shown that it is sufficient for the X-ray source to rotate around a minimum angle which is less than 360° during the scan. A scan involving such a rotation of the X-ray is usually also referred to as short scan. More specifically, it can be shown that the minimum angle is 180°+ fan angle, where the fan angle corresponds to the full opening angle of the fan beam.

In case of a short scan with a centered detector, some lines passing through the object are likewise sampled redundantly as in case of a full 360° scan, while other lines are only sampled once. Redundant projection values are particularly acquired at the start and the end of the arc, and non-redundant projection values are particularly acquired in the middle section of the arc. In order to take account of this redundancy pattern, it is likewise possible to perform a weighting of the measured projection values in the process of reconstructing the image.

In principle this could be achieved by weighting the non-redundantly measured projection values with 1 and weighting one projection value of each redundant value pair also with 1 and the other value of the redundant value pair with κ. However, such a sharp binary weighting function results in image artifacts. These artifacts can be avoided by using a smooth weighting function. One example of such a weighting function is known as Parker weighting and particularly described in the publication S. Wesarg et al., "Parker weights revisited", Med. Phys. 29 (3), March 2002.

The weighting function particularly depends on the length of the arc traversed by the focus point of the X-ray beam. In practical implementations, this arc length usually deviates from its nominal value resulting from the specified nominal start and end positions of the X-ray source due to inaccuracies occurring in the operation of the X-ray tomography system. Such deviations can particularly result from inaccuracies in the realization of specified nominal positions for the X-ray source, which can be caused by hysteresis in the employed X-ray tomography system and/or by other effects. Further, such deviations can result from an imperfect synchronization between the X-ray source and the gantry, for example, which e.g. result in delayed activation of the X-ray source with respect to the start of the gantry rotation. Due to these deviations the actual arc length of the trajectory of the focus point has to be determined in order to perform the redundancy weighting and avoid related image artifacts.

In such a way, a three-dimensional image of a complete object can be generated by performing a short scan. However, this requires that the X-ray beam as incident into the detector illuminates the whole object. Otherwise, i.e. if the X-ray beam only illuminated part of the object, truncation artifacts will occur in the generated images. This requirement particularly results in a certain minimum size of the detector.

In order to increase the size of the field-of-view for a given detector size, the detector may be positioned off-center. This means that the detector is positioned asymmetrically with respect to the central ray of the beam passing through the isocenter. The asymmetric positioning of the detector leads to truncated projections, since the fan beam as incident onto the detector does not illuminate the whole object on one side of the central ray. However, the object can be completely sampled when two short scans are carried out in which the X-ray source travels on overlapping arcs and when the detector offset with respect to the central ray is switched from one side to the other between the two short scans. In order to efficiently carry out these two short scans, the X-ray source may be rotated in one direction for carrying out the first short scan and back in the other direction for carrying out the other short scan, where the end position of the first scan may nominally corresponds to the start position of the second scan.

On the basis of the projection data acquired during two short scans carried out using an off-center detector by moving the X-ray source along overlapping arcs, a three-dimensional image of an object in an extended field-of-view can be reconstructed. In order to avoid related image artifacts, a redundancy weighting also has to be carried out in this acquisition scheme. In this respect, redundancies have to be compensated for, which occur to due a sampling of the same lines in both scans. Likewise, redundancies have to be compensated for, which occur due to the redundant sampling of lines in each scan. These redundancies correspond to those also occurring in the case of a single short scan and giving cause to the Parker weighting.

SUMMARY OF THE INVENTION

It is an object of the invention to provide for a redundancy weighting of projection data acquired by means of an off-center detector during two short scans, particularly with respect to redundancies resulting from a redundant sampling of lines in each short scan.

In one aspect, the invention suggests a device for off-center detector X-ray tomography reconstruction of an image of an object on the basis of projection data, wherein the projection data is acquired by means of the off-center detector during a rotation of an X-ray source and the off-center detector around the object in two rotational passes of less than 360°, the X-ray source generating a diverging X-ray beam having a focus point and the focus point travelling along largely overlapping arcs in the two rotational passes, the off-center detector being positioned asymmetrically with respect to a central ray of the X-ray beam and a direction of a detector offset being reversed between the passes. The device is configured for redundancy weighting of the projection data with respect to a redundant acquisition of projection values during each of the rotational passes using a redundancy weighting function, the redundancy weighting functions being determined on the basis of a union of the arcs.

Since the redundancy weighting of projection values acquired in the first and second rotational pass is made on the basis of a uniform redundancy weighting function, which is determined on the basis of the union of the arcs traversed by the focus point of the X-ray beam in the first rotational pass and the second rotational pass, high-quality images can be reconstructed. The term union of the arcs particularly denotes an arc consisting of the points contained in at least one of the arcs traversed by the focus point in the two rotational passes. The redundancy weighting function may particularly be a Parker weighting function.

In accordance with a straightforward solution to the redundancy weighting problem, it would also be possible to determine individual redundancy weighting functions for each of the rotational passes on the basis of the length of the arc traversed by the focus point of the X-ray beam in the respective rotational pass. However, it turned out that this solution leads to artifacts in the reconstructed image. These artifacts can be avoided when a uniform redundancy weighting function is used for redundancy weighting the projection values acquired in both rotational passes, which is determined based on the union of the arcs traversed by the focus point of the X-ray beam in the first and second rotational passes.

In one embodiment of the invention, the device is configured to determine the redundancy weighting function based on a parameter representing a length of the union of the arcs. The parameter may particularly correspond to the angular distance between the end points of the union of the arc. For a given distance between the focus point of the X-ray beam and the isocenter of the rotation of the X-ray source and the detector, this angular distance parameterizes the length of the union of the arc. In case of a circular trajectory of the focus point of the X-ray beam, this distance is constant. However, the invention is not limited to such circular trajectories and is also applicable to scans involving a varying distance between the focus point of the X-ray beam and the isocenter.

In one embodiment, the parameter is determined based on measured positions of the X-ray source at the start and the end of each rotational pass. This ensures that the redundancy weighting function is determined on the basis of the actual length of the union of the arcs traversed by the focus point of the X-ray source in the rotational passes of the scan to be evaluated.

However, the redundancy weighting function can only be determined after completion of the scan in this embodiment so that image reconstruction can only start after completion of the scan. Therefore, a further embodiment of the invention includes that the parameter is pre-stored in the device for nominal positions of the X-ray source at the start and end of the first and second rotational passes based on a value of the parameter empirically determined for the nominal positions. This value of the parameter may particularly be determined in a calibration scan carried out beforehand.

As the deviation between the nominal start and end positions of the X-ray source in the rotational passes and the actual start and end positions is essentially the same in different scans, the pre-stored value of the parameter essentially corresponds to the actual value of the parameter in the scan to be evaluated. Hence, an accurate image reconstruction can be carried out and the image reconstruction can start during the scan, so that the reconstructed image is available quickly after completion of the scan.

In an alternative embodiment, the device is configured to use an estimated value of the parameter, which represents an estimated length of the union of the arcs which is equal to or larger than the union of the actual arcs. Such a value can be determined based on the nominal length of the union of the arcs traversed by the focus point of the X-ray beam and an additional safety margin added to the nominal length. In this embodiment, it can be ensured that at least an approximated redundancy weight can be calculated for each line during the first and second rotational passes of the scan without having to measure the actual start and end positions of the X-ray source in the first and second rotational passes during the scan or beforehand.

In a further embodiment of the invention, the diverging X-ray beam incident onto the off-center detector has an opening angle which corresponds to a sum of a first opening angle and a second opening angle between edge rays and a central ray, and wherein the focus point of the X-ray beam is rotated by a rotation angle, which is equal to or larger than the sum of 180° and twice the larger opening angle, in each rotational pass. Hereby, it can be ensured that all lines through the field-of-view are sampled during the scan. The central ray corresponds to the ray of the X-ray beam, which passes through the center of the field-of-view. This center is usually also referred to as isocenter and corresponds to the center of the rotation of the X-ray source in case of a circular trajectory of the X-ray source.

Moreover, an embodiment of the invention includes that nominal rotation angles of the focus point of the X-ray beam during the first and second rotational passes correspond to each other. Thus, the focus point travels by the same angular distance in the first and second rotational passes.

In one embodiment of the invention, the detector offset has a first direction and a first magnitude during the first rotational pass and a second direction and magnitude during the second rotational pass, the second magnitude corresponding to the first magnitude and the second direction being opposite to the first direction.

In a further embodiment of the invention, the X-ray source is rotated in a first direction during the first rotational pass and in a second direction during the second rotational pass, the second direction being opposite to the first direction. In a related embodiment of the invention, a nominal start position of the second rotational pass corresponds to a nominal end position of the first rotational pass. These embodiments allow for an especially time-efficient execution of the two rotational passes.

In one embodiment, the device is further configured for redundancy weighting of the projection data with respect to a redundancy due to an acquisition of the same projection values in both rotational passes. This redundancy may particularly be taken account for by an additional redundancy weighting function.

Moreover, one embodiment of the invention comprises that the diverging X-ray beam is configured as a fan beam or a cone beam.

In a further aspect, the invention suggests a method for off-center detector X-ray tomography reconstruction of an image of an object on the basis of projection data, wherein the projection data is acquired by means of the off-center detector during a rotation of an X-ray source and the off-center detector around the object in two rotational passes of less than 360°, the X-ray source generating a diverging X-ray beam having a focus point and the focus point travelling along largely overlapping arcs in the two rotational passes, the off-center detector being positioned asymmetrically with respect to a central ray of the X-ray beam and a direction of a detector offset being reversed between the passes. The method comprises redundancy weighting of the projection data with respect to a redundant acquisition of projection values during each of the rotational passes using a redundancy weighting function, the redundancy weighting functions being determined on the basis of a union of the arcs.

In a further aspect, the invention suggests a computer program for off-center detector X-ray tomography reconstruction, comprising program code means for causing a computer to carry out the method when the computer program is run on the computer.

It shall be understood that the device of claim 1, the method of claim 14 and the computer program of claim 15 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

BRIEF DESCRIPTION OF THE DRAWINGS

In the following drawings:

FIG. 1 schematically and exemplarily shows components of an X-ray tomography system for acquiring projection data using an off-center X-ray detector, FIG. 2 schematically and exemplarily illustrates an off-center detector geometry, FIG. 3a schematically and exemplary illustrates the start and end positions of a first rotational pass of a two-pass X-ray tomography scan and a trajectory of a focus point of an X-ray beam during the first rotational pass, FIG. 3b schematically and exemplary illustrates the start and end positions of a second rotational pass of the two-pass scan and a trajectory of the focus point of the X-ray beam during the second rotational pass, FIG. 4 schematically and exemplarily shows trajectories of a focus point of an X-ray beam during a first rotational pass and a second rotational pass of a two-pass CT scan, and FIG. 5 schematically and exemplarily shows a diagram illustrating regions comprising redundantly acquired projection data.

DETAILED DESCRIPTION OF EMBODIMENTS

Figure 1:
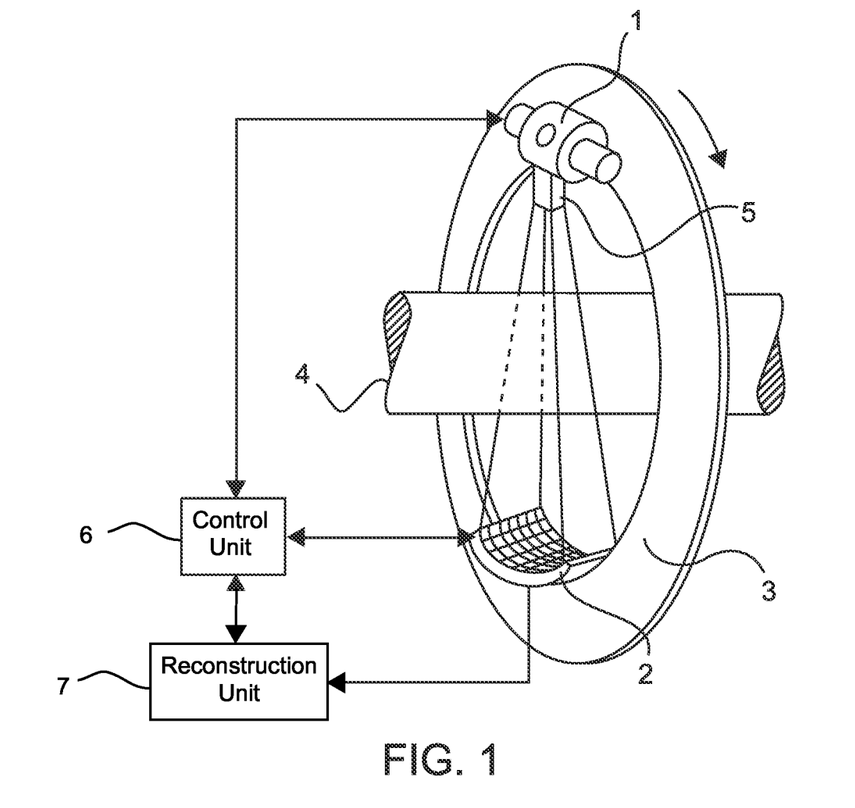

FIG. 1 schematically and exemplarily show components of an X-ray tomography system for carrying out off-center detector X-ray tomography scans in two rotational passes and to reconstruct three-dimensional images from projection data acquired in such scans. The image reconstruction is based on a redundancy weighting of projection values particularly with respect to a redundant acquisition of projection values in each of passes, where this redundancy weighting is performed on the basis of a uniform weighting function for both passes, which is determined on the basis of the trajectories of the focus point in both rotational passes.

The X-ray tomography system comprises an X-ray source 1, such as an X-ray tube, and an X-ray detector 2, which are mounted opposite to each other on a rotatable gantry 3. The rotatable gantry 3 may be configured as annular device, a C-arm, or it may be realized by two robotic arms, for example. By rotating the rotatable gantry 3, the X-ray source 1 and the X-ray detector 2 can be rotated around on object to be imaged, which is positioned in a measurement region 4 located between the X-ray source 1 and the X-ray detector 2. The X-ray source 1 is configured to produce a divergent X-ray beam, which may particularly be configured as fan beam or a cone beam. In order to form the X-ray beam in accordance with the desired shape, the X-ray source 1 may particularly comprise a suitable collimator 5. The X-ray detector 2 comprises a curved or flat detector array consisting of a plurality of detector elements for measuring incident X-ray radiation. During operation, the radiation measurement of each detector element at a certain position of the X-ray detector 2 corresponds to one projection value of the object to be imaged with respect to a line corresponding to the path of the of the part of the X-ray beam incident onto the respective detector element.

Figure 2:
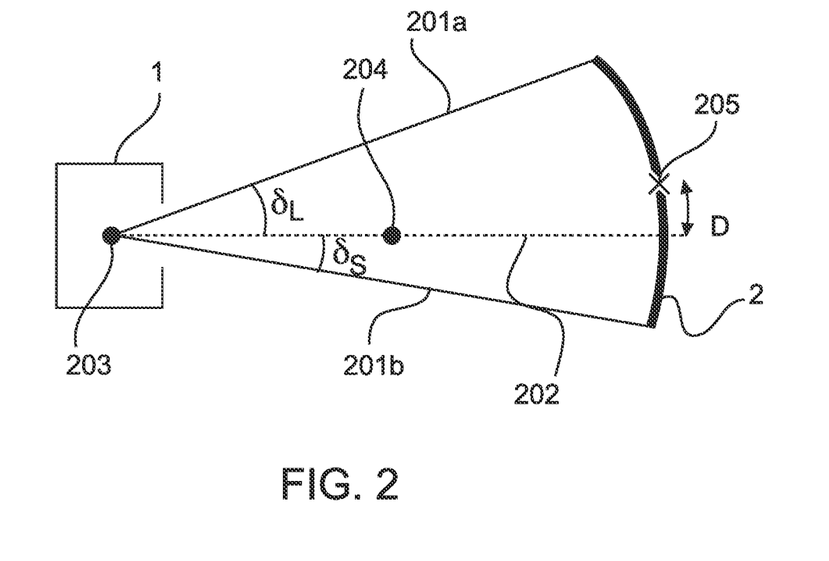

During the X-ray scans carried out in the system, the X-ray detector 2 is operated as an off-center detector. This means that the detector array of the X-ray detector 2 is positioned asymmetrically with respect to the central ray of the beam passing through the isocenter, in a direction perpendicular to the direction of the central ray. In other words, the central ray through the isocenter does not correspond to the bisecting line of the fan beam incident onto the X-ray detector 2. Rather, the beam has an opening angle that is composed of two different angles $\delta_L$ and $\delta_S$, with $\delta_L > \delta_S$, between the central ray and the edge rays on both sides of the central ray. This geometry is schematically and exemplarily illustrated in FIG. 2, showing the angles $\delta_L$ and $\delta_S$ between the edges rays 201a, 201b and the central ray 202 passing from the focus point 203 of the X-ray beam through the isocenter 204. The detector offset, which may be parameterized by the displacement D between the middle 205 of the X-ray detector 2 and the central ray 202 of the X-ray beam, can preferably be controlled by displacing the detector array relative to X-ray source 1 until the desired detector offset is achieved. Further, the shape of the X-ray beam may be adapted to a selected detector offset such that the X-ray detector 2 is fully illuminated and that essentially no X-ray radiation reaches regions next to the X-ray detector 2. This may be achieved by means of a suitable configuration of the collimator 5 included in the X-ray source 1.

The components of the X-ray tomography system including the X-ray source 1, the rotatable gantry 3 and the X-ray detector 2 are controlled by means of a control unit 6, which may be configured as a computer-implemented unit comprising a computer program which includes procedures for controlling the components of the X-ray tomography system and which is executed in a computer device connected to the components of the X-ray tomography system in a suitable way.

In order to reconstruct images from the projection data acquired by means of the X-ray detector 2, the X-ray tomography system comprises a reconstruction unit 7. Also the reconstruction unit 7 may be a computer-implemented unit which comprises a computer program that provides procedures for reconstructing the three-dimensional images and that is executed on the aforementioned computer device or a further computer device connected to the X-ray detector 2. In one embodiment, the acquired projection values may be transmitted to the reconstruction unit 7 as soon as they are available in the X-ray detector 2. In this embodiment, the reconstruction unit 7 may reconstruct an image on the fly, while the X-ray tomography scan is carried out. This has the advantage that the image is quickly available upon the completion of the scan.

Using the off-center X-ray detector 2, the X-ray tomography system carries out a tomography scan in two rotational passes in which the focus point 203 of the X-ray beam travels along overlapping arcs. In order to sample all lines through the object to be imaged, the focus point 203 is rotated around the isocenter 204 by an angle of at least $180°+2\delta_L$ during each rotational pass and the detector offset is switched between the rotational passes. In so doing, the detector offset is preferably changed such that the magnitude of the detector offset is maintained and the direction of the detector offset is reversed. Thus, the angles $\delta_L$ and $\delta_S$ effectively changes sides with respect to the central ray of the X-ray beam. In such a way, images can be generated for a field-of-view which corresponds to the field-of-view of a centered detector capturing an X-ray beam having an opening angle of $2\delta_L$.

Figure 3A:
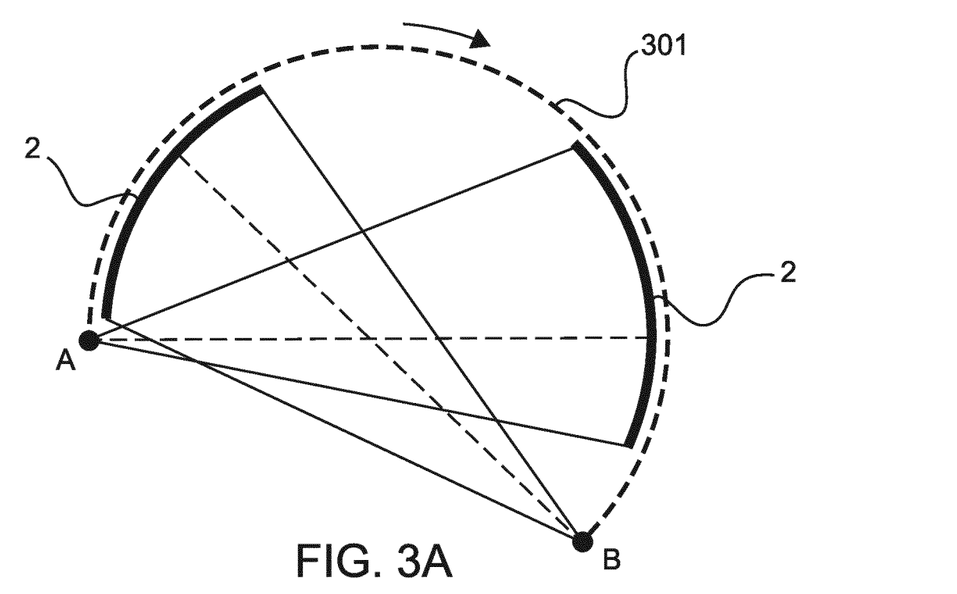
Figure 3B:
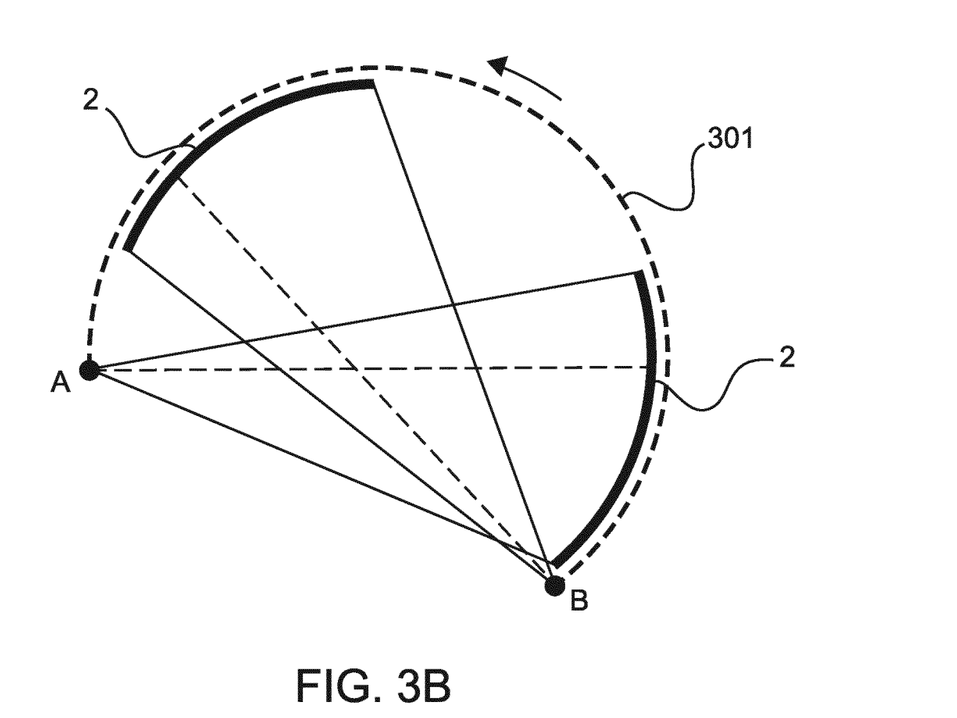

Nominally, the focus point 203 of the X-ray beam preferably travels along identical arcs during the first and second rotational passes. Moreover, the end position of the first rotational pass preferably corresponds to the start position of the second rotational pass in one embodiment in order to minimize the scan time. Thus, as schematically and exemplarily shown in FIG. 3a, the focus point 203 travels from a start position A along an arc 301 to the position B in the first rotational pass, where the angular distance between the position A and the position B is $180°+2\delta_L$ (or larger). Then, upon having switched the detector offset, the focus point 203 travels from the position B back to the position A along the same arc 301 in the second rotational pass, as schematically and exemplarily illustrated in FIG. 3b.

Figure 4:
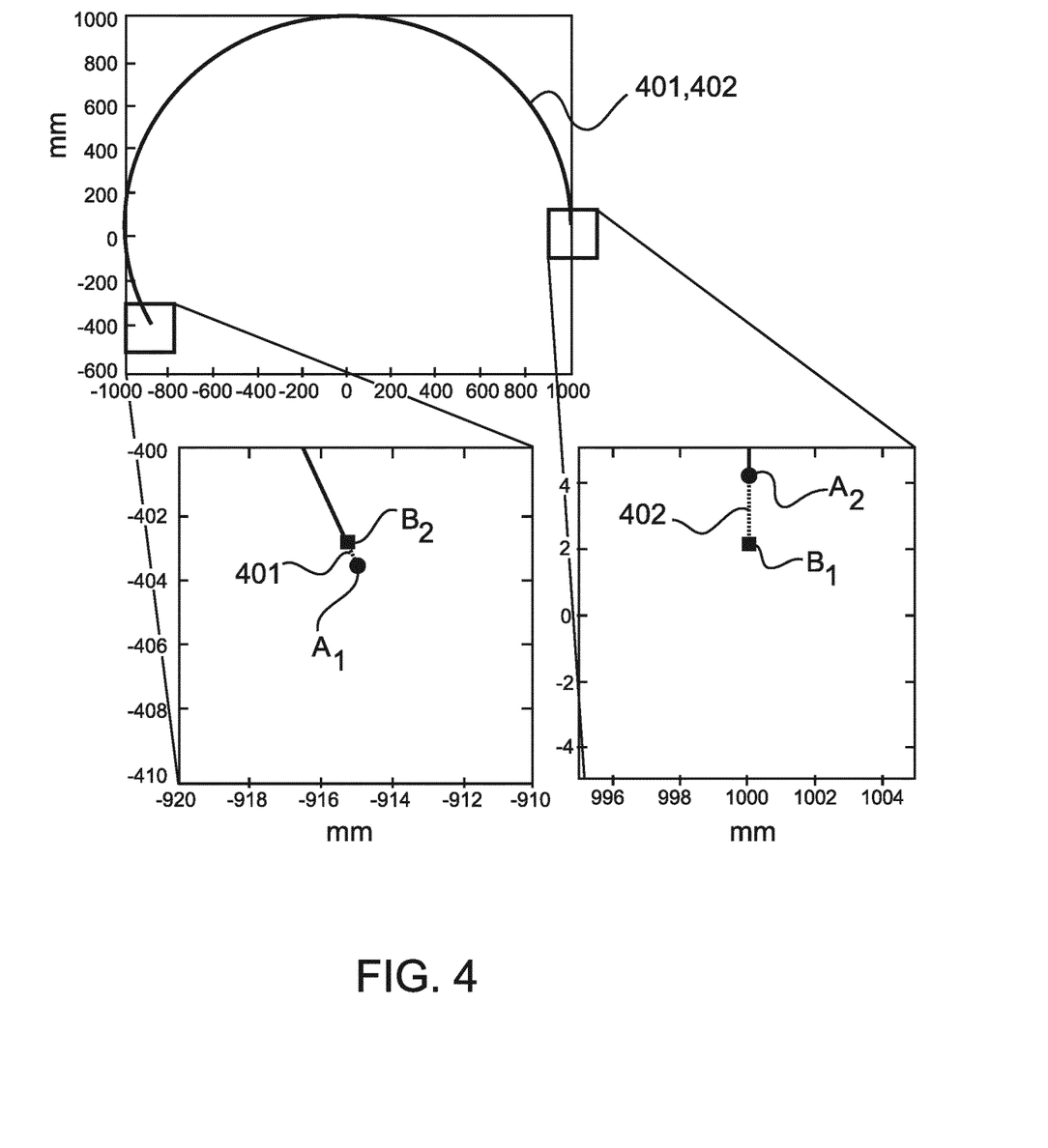

In practice, the actual start position of the focus point 203 for the second rotational pass deviates from the end position of the focus point 203 after the first rotational pass start and the actual end position of the focus point 203 after the second rotational pass deviates from the start position of the focus point 203 in the first rotational pass. This is schematically and exemplarily illustrated in FIG. 4, showing a trajectory 401 and a trajectory 402 of the focus point 203 during the first and second rotational pass. As can be seen in the figure, the first trajectory 401 and the trajectory 402 are largely overlapping. However, the start position $A_1$ of the focus point 203 in the first rotational pass deviates slightly from the end position $B_2$ of the focus point 203 in the second rotational pass, and the start position $B_1$ of the focus point 203 in the second rotational pass deviates slightly from the end position $A_2$ of the focus point 203 in the first rotational pass.

As explained above, these deviations result from inaccuracies occurring in the operation of the X-ray tomography system, such as inaccuracies in the realization of specified nominal positions for the X-ray source 1 and/or an imperfect synchronization between the X ray source 1 and the rotatable gantry 3.

In order to reconstruct an image on the basis of the projection data acquired in the aforementioned two-pass scan, the reconstruction unit 7 applies a suitable reconstruction algorithm known to a person skilled in the art. Exemplary reconstruction algorithms, which may be applied in case the X-ray beam is configured as a cone beam, are described in the publication D. Schäfer et al., "FBP and BPF reconstruction methods for circular X-ray tomography with off-center detector", Med. Phys. 38 (7), July 2011. In case the X-ray beam is configured as a fan beam, the reconstruction unit 7 may apply a suitable adaptation of these algorithms to the fan beam shape, which corresponds to a special case of the more general cone beam shape.

The image reconstruction is carried out on the basis of redundancy weighted projection data $w_i(\alpha, \beta) g_i(\alpha, \beta)$. Here, $g_i(\alpha, \beta)$ denotes a projection value acquired by measuring a ray having an angle $\alpha$ within the fan at a source angle $\beta$ in the i-th rotational pass (i=1, 2), where the angle $\alpha$ within the fan, may correspond to the angle between the ray and the central ray, and where the source angle corresponds to the angle between the central ray and a reference (in case of a cone beam, also a cone-beam variable is assigned to the projection values, which is not made explicit herein). The parameters $w_i(\alpha, \beta)$ denote values of a redundancy weighting function for the i-th rotational pass.

The redundancy weighting functions take account of the redundant sampling of lines during the X-ray tomography scan. As will be explained in more detail herein below, they particularly compensate for a redundant sampling of lines within each rotational pass of the scan. Preferably, they also compensate for a redundant sampling of lines in both rotational passes of the scan. In this case, each of the redundancy weighting functions may correspond to a product of a first redundancy weighting function $w_{ai}$ and a second redundancy weighting function $w_{bi}$, where the first redundancy weighting function $w_{ai}$ takes account of the redundant sampling of lines within the i-th rotational pass and the second redundancy weighting function $w_{bi}$ takes account of the remaining redundancy due to the redundant sampling of lines in both rotational passes.

The second redundancy weighting function $w_{bi}$ may be derived based on the overlap of the off-center detector at a source angle in the first pass and the off-center detector at the same source angle in the second rotational pass and, thus, only depends on the angle $\alpha$. A suitable redundancy weighting function is particularly disclosed in the aforementioned publication by D. Schäfer et al. for an image reconstruction from projection data acquired by means of an off-center detector in a full 360° scan, and this weighting function may also be applied in case of the present two-pass scan.

In the following, the first redundancy weighting functions will be further discussed and, suppressing the index a, these weighting functions will be denoted as $w_i(\alpha, \beta)$ in this discussion. As said, the weighting function $w_i(\alpha, \beta)$ compensates for the redundant sampling of lines in the i-th rotational pass.

In this respect, it is known that $g_i(\alpha, \beta) = g_i(-\alpha, \beta + 180° + 2\alpha)$. In case of a centered detector and a fan opening angle $\delta$, this equation leads to the diagram shown in FIG. 5 for a scan over a range of $180° + 2\delta + 2\varepsilon$ where $2\varepsilon$ is also referred to as overscan angle as it corresponds to the extension beyond the minimum range of $180° + 2\delta$. In the diagram, the areas I and I' contain redundant data and the regions II and II' contain redundant. By way of example, three markers are shown in the diagram, where identical markers indicate redundant rays. Region III does not contain redundant data.

Figure 5:
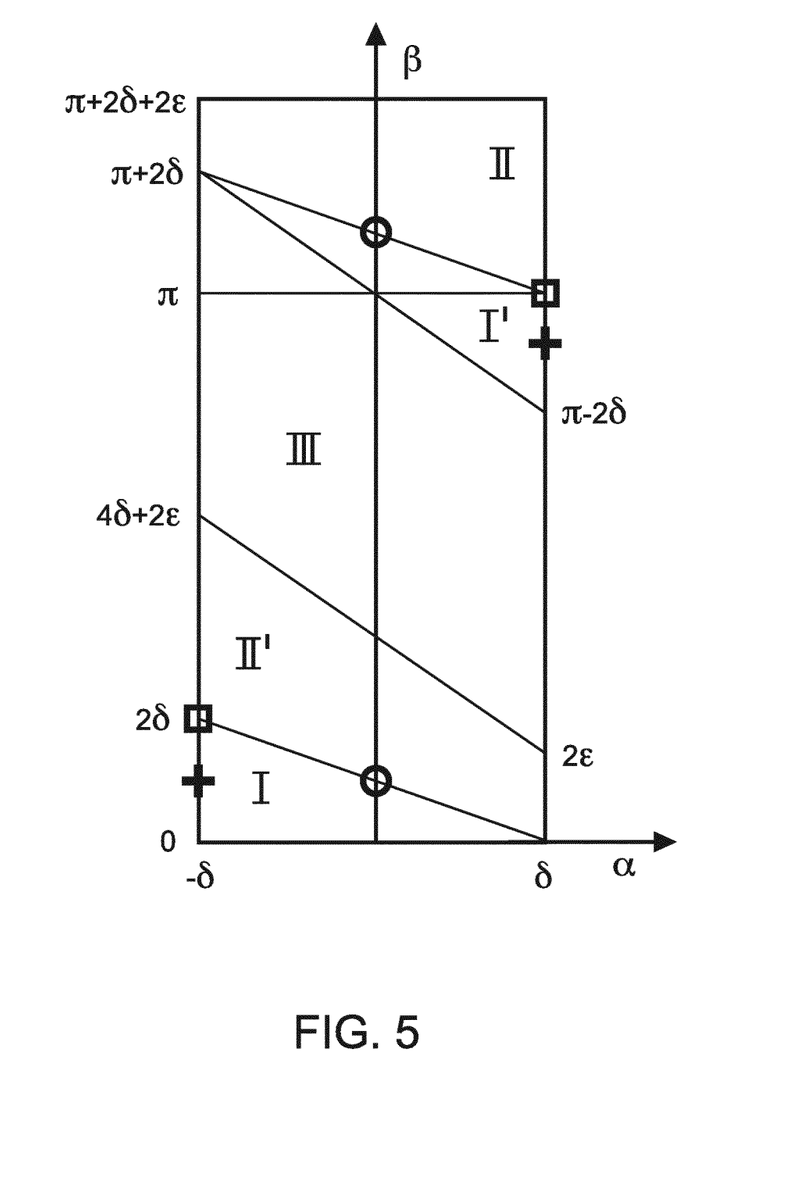

In principle, it would be possible to assign a redundancy weight of 1 to the rays in the regions I', II' and III in the diagram of FIG. 5 and a redundancy weight of 0 to the rays in the regions I and II in order to solve the redundancy problem. However, this choice would lead to increased noise in the image and to image artifacts when using standard image reconstruction techniques. These artifacts can be avoided by using a smooth redundancy weighting function. Such weighting function may particularly depend on a parameter representing the length of arc traversed by the focus point 203 of the X-ray beam during the scan or pass. This parameter may particularly be the angular range or distance $180° + 2\delta + 2\varepsilon$.

One example of such a weighting function is the Parker weighting function. Using $\gamma = \pi + 2\delta + 2\varepsilon$ (with $\pi$ representing an angle of 180°) as the parameter representing the length of the arc traversed by the focus point 203 of the X-ray beam, this function can be written as:

$$w_p(\alpha, \beta; \gamma) = \begin{cases} \sin^2\left(\frac{\pi}{2} \cdot \frac{\beta}{\gamma - \pi - 2\alpha}\right), & 0 \le \beta < \gamma - \pi - 2\alpha \\ 1, & \gamma - \pi - 2\alpha \le \pi - 2\alpha \\ \sin^2\left(\frac{\pi}{2} \cdot \frac{\gamma - \beta}{\gamma - \pi - 2\alpha}\right), & \pi - 2\alpha < \beta \le \gamma \end{cases}$$

Using such a weighting function, a straightforward choice for the redundancy weighting functions $w_i$ for the two-pass scan would be $w_i = w_p(\alpha, \beta; \gamma_i)$, where the parameters $\gamma_i$ corresponds that actual lengths of the arcs traversed by the focus point 203 of the X-ray beam during the first and second rotational pass. Thus, $\gamma_1$ corresponds to the angular distance between the positions $A_1$ and $A_2$ shown in FIG. 4, i.e. to the angle between the connection lines connecting the positions $A_1$ and $A_2$ with the isocenter. Further, $\gamma_2$ corresponds to the angular distance between the positions $B_1$ and $B_2$ shown in FIG. 4. This choice for the redundancy weighting functions corresponds to a separate calculation of the redundancy weightings for each of the two rotational passes of the scan.

However, it turned out that this choice for the redundancy weighting functions leads to streak artifacts in the reconstructed images.

In order to avoid these artifacts, the invention suggests to use a uniform redundancy weighting function for the redundancy weighting of projection data of both rotational passes of the scan and to determine this redundancy weighting function based on the union of the arcs traversed by the focus point 203 of the X-ray beam during the first rotational pass and the second rotational pass. More specifically, the redundancy weighting function is determined based on a parameter representing a length of the union of the arcs traversed by the focus point 203 of the X-ray beam during the first rotational pass and the second rotational pass. The union of these arcs is to be understood to denote an arc consisting of points contained in at least one of these arcs. Thus, the redundancy weighting function is determined on the basis of the full arc, which is traversed by the focal point of the X-ray beam in both rotational passes. Moreover, a uniform redundancy weighting function is used, which means that the same redundancy weighting function is used for redundancy weighting projection values acquired in the first pass and the second pass of the scan.

The angular range of the union of the arcs traversed by the focus point 203 of the X-ray beam in the first and second rotational pass may be denoted as $\gamma_{12}$ and may be given by $\gamma_{12} = \pi + 2\delta_L + 2\varepsilon_{12}$. In this expression $\delta_L$ denotes the larger angle between the central ray and an edge ray of the asymmetric X-ray beam incident onto the X-ray detector 2 as explained above and $\varepsilon_{12}$ denotes the cumulated overshoot over the angular range $180° + 2\delta_L$ in both rotational passes. Using this nomenclature and using the exemplary redundancy weighting function $w_p$ given above, the first redundancy weighting function and the second redundancy weighting function for redundancy weighting of the projection data acquired during the first rotational pass and the second rotational pass of the two-pass scan may be determined as $w_1 = w_2 = w_p(\alpha, \beta; \gamma_{12})$ in one embodiment of the invention.

In the example shown in FIG. 4, the union of the arcs traversed by the focus points of the X-ray beam in the first rotational pass and the second rotational pass corresponds to the arc between the points $A_1$ and $B_1$. The value of the parameter $\gamma_{12}$ therefore corresponds to the angular distance between the points $A_1$ and $B_1$.

In order to reconstruct an image on the basis of a redundancy weighting function of the aforementioned type, the reconstruction unit 7 determines the function on the basis of the union of the arcs traversed by the focus of the X-ray beam. In particular, the reconstruction unit 7 determines the function on the basis of the relevant parameter representing the length of the union of arc, which may particularly correspond to the angular range covered by the union of the arcs as explained above.

In one embodiment, the reconstruction unit 7 determines the relevant parameter on the basis of the actual start position and the actual end position of the X-ray source 1 in the first rotational pass and the second rotational pass. These positions may be measured by a suitable localization system integrated into the X-ray tomography system. Typically, X-ray tomography systems dispose of such a localization system by default and log selected or all positions of the X-ray source 1, in which radiation measurements are carried out, in a measurement protocol. This measurement protocol may be evaluated by the reconstruction unit 7 in order to determine the relevant parameter.

However, the redundancy weighting function can only be determined after completion of the scan in this approach, since the end position of the X-ray source in the second rotational pass can only be measured at the end of the scan. Thus, image reconstruction can only start after completion of the scan.

In order to be able to start image reconstruction already during the scan, the reconstruction unit 7 may use a value of the relevant parameter, which is pre-stored in the reconstruction unit 7, in a further embodiment. This value may be determined in a calibration scan, which is carried out beforehand in the same way as the scan to be evaluated using the same nominal start and end positions of the X-ray source 1 in the first and second rotational pass. For this calibration scan, the value of the relevant parameter is determined on the basis of the measured actual start and end positions of the X-ray source 1 in the first end second rotational pass and this value is then stored in the reconstruction unit 7. Since it is to be assumed that the deviation between the relevant nominal positions of the X-ray source 1 and the actual positions is essentially the same for the calibration scan and any later scan, the stored value of the parameter accurately corresponds to the actual value of the parameter in the scan to be evaluated.

In an alternative embodiment, the reconstruction unit 7 estimates the value of the parameter on the basis of the nominal start and end positions of the X-ray source 1 in the first and second rotational passes of the scan to be evaluated. For this purpose, the reconstruction unit 7 may calculate a value of the parameter from the nominal positions and add a suitable safety margin to the calculated value. The safety margin may be a pre-configured value which is preferably selected such that the estimated value of the parameter represents a length of the union of the arc which is not shorter than the actual length of the union of the arc. Further, the safety margin may preferably be selected such that the estimated value of the parameter represents a length of the union of the arc which is not much longer than the actual length of the union of the arc. In such a way, it can be ensured that a redundancy weight can be calculated for each sampled line, which is at least approximately accurate.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A device for off-center detector X-ray tomography reconstruction of an image of an object on a basis of projection data, the device comprising:
   an X-ray source configured to generate a diverging X-ray beam having a focus point;
   an off-center X-ray detector configured to acquire projection data, wherein the off-center X-ray detector is positioned asymmetrically with respect to a central ray of the diverging X-ray beam;
   a rotatable gantry, wherein the X-ray source and the off-center X-ray detector are mounted opposite to each other on the rotatable gantry;
   a controller configured to rotate the rotatable gantry such that the X-ray source and the off-center X-ray detector are rotated around an object in two rotational passes of less than 360°, the focus point traveling along largely overlapping arcs in the two rotational passes, wherein a direction of an offset of the off-center X-ray detector is reversed between the two rotational passes;
   a processor; and
   a tangible, non-transitory computer-readable medium that stores instructions, which when executed by the processor, cause the processor to redundancy weight the projection data with respect to an acquisition of the projection data during each rotational pass of the two rotational passes using a redundancy weighting function, wherein the redundancy weighting function is determined on a basis of a union of the largely overlapping arcs in the two rotational passes.

2. The device as defined in claim 1, wherein the instructions, when executed by the processor, further cause the processor to determine the redundancy weighting function based on a parameter representing a length of the union of the largely overlapping arcs in the two rotational passes.

3. The device as defined in claim 2, wherein the parameter representing a length of the union of the largely overlapping arcs in the two rotational passes is pre-stored in the tangible, non-transitory computer-readable medium for nominal positions of the X-ray source at a start and at an end of a first rotational pass and a second rotational pass of the two rotational passes based on a value of the parameter empirically determined for the nominal positions.

4. The device as defined in claim 2, wherein the instructions, when executed by the processor, further cause the processor to determine the parameter based on measured positions of the X-ray source at a start and at an end of each rotational pass of the two rotational passes.

5. The device as defined in claim 2, wherein the instructions, when executed by the processor, further cause the processor to use an estimated value of the parameter, which represents an estimated length of the union of the largely overlapping arcs in the two rotational passes, which is equal to or larger than a union of actual largely overlapping arcs.

6. The device as defined in claim 1, wherein the redundancy weighting function comprises a Parker weighting function.

7. The device as defined in claim 1, wherein the X-ray source is configured to generate diverging X-ray beam, which is incident onto the off-center X-ray detector, has an opening angle which corresponds to a sum of a first opening angle and a second opening angle between edge rays and the central ray, and wherein the focus point of the diverging X-ray beam is rotated by a rotation angle, which is equal to or larger than a sum of 180° and twice a larger opening angle of the first opening angle and the second opening angle in each rotational pass of the two rotational passes.

8. The device as defined in claim 7, wherein nominal rotation angles of the focus point of the diverging X-ray beam during a first rotational pass and a second rotational pass of the two rotational passes correspond to each other.

9. The device as defined in claim 1, wherein the offset of the off-center X-ray detector has a first direction and a first magnitude during a first rotational pass of the two rotational passes and a second direction and a second magnitude during a second rotational pass of the two rotational passes, the second magnitude corresponding to the first magnitude and the second direction being opposite to the first direction.

10. The device as defined in claim 1, wherein the controller is configured to rotated the rotatable gantry so that the X-ray source and the off-center X-ray detector are rotated in a first direction during a first rotational pass of the two rotational passes and in a second direction during a second rotational pass of the two rotational passes, the second direction being opposite to the first direction.

11. The device as defined in claim 10, wherein a nominal start position of the second rotational pass corresponds to a nominal end position of the first rotational pass.

12. The device as defined in claim 1, wherein the instructions, when executed by the processor, further cause the processor to redundancy weight the projection data with respect to a redundancy due to an acquisition of a same projection data in both rotational passes of the two rotational passes.

13. The device as defined in claim 1, further comprising a collimator adapted to shape the diverging X-ray beam as a fan beam or a cone beam.

14. A method for off-center detector X-ray tomography reconstruction of an image of an object on a basis of projection data, the method comprising:
   acquiring projection data during a rotation of an X-ray source and an off-center X-ray detector around an object in two rotational passes of less than 360°, wherein: the X-ray source has a focus point configured to generate a diverging X-ray beam; the focus point travels along largely overlapping arcs in the two rotational passes; the off-center X-ray detector is positioned asymmetrically with respect to a central ray of the diverging X-ray beam; and a direction of an offset of the off-center X-ray detector is reversed between the two rotational passes; and
   redundancy weighting the projection data with respect to an acquisition of the projection data during each rotational pass of the two rotational passes using a redundancy weighting function, wherein the redundancy weighting function is determined on a basis of a union of the largely overlapping arcs in the two rotational passes.

15. A tangible non-transitory computer-readable medium that stores instructions, which when executed by a processor, cause the processor to:
   acquire projection data during a rotation of an X-ray source and an off-center X-ray detector around an object in two rotational passes of less than 360°, wherein: the X-ray source has a focus point configured to generate a diverging X-ray beam; the focus point travels along largely overlapping arcs in the two rotational passes; the off-center X-ray detector is positioned asymmetrically with respect to a central ray of the diverging X-ray beam; and a direction of an offset of the off-center X-ray detector is reversed between the two rotational passes; and
   redundancy weight the projection data with respect to an acquisition of the projection data during each rotational pass of the two rotational passes using a redundancy weighting function, wherein the redundancy weighting function is determined on a basis of a union of the largely overlapping arcs in the two rotational passes.

16. The tangible non-transitory computer-readable medium as defined in claim 15, wherein the instructions, when executed by the processor, further cause the processor to determine the redundancy weighting function based on a parameter representing a length of the union of the largely overlapping arcs in the two rotational passes.

17. The tangible non-transitory computer-readable medium as defined in claim 16, wherein the parameter is pre-stored in the tangible non-transitory computer-readable medium for nominal positions of the X-ray source at a start and at an end of a first rotational pass and a second rotational pass of the two rotational passes based on a value of the parameter empirically determined for the nominal positions.

18. The tangible non-transitory computer-readable medium as defined in claim 16, wherein the instructions, when executed by the processor, further cause the processor to determine the parameter based on measured positions of the X-ray source at a start and at an end of each rotational pass of the two rotational passes.

19. The tangible non-transitory computer-readable medium as defined in claim 16, wherein the instructions, when executed by the processor, further cause the processor to use an estimated value of the parameter, which represents an estimated length of the union of the largely overlapping arcs in the two rotational passes, which is equal to or larger than a union of actual largely overlapping arcs in the two rotational passes.

20. The tangible non-transitory computer-readable medium as defined in claim 15, wherein the redundancy weighting function comprises a Parker weighting function.

* * * * *